United States Patent
Colin et al.

(10) Patent No.: US 8,613,217 B2
(45) Date of Patent: Dec. 24, 2013

(54) METHOD AND APPARATUS FOR DETERMINING THE INTERFACIAL TENSION BETWEEN TWO LIQUIDS

(75) Inventors: Annie Colin, Bordeaux (FR); Pierre Guillot, Crolles (FR); Armand Ajdari, Paris (FR)

(73) Assignees: Rhodia Operations, Aubervilliers (FR); Universite de Bordeaux I, Talence (FR)

( * ) Notice: Subject to any disclaimer, the term of this patent is extended or adjusted under 35 U.S.C. 154(b) by 574 days.

(21) Appl. No.: 12/934,023

(22) PCT Filed: Mar. 24, 2009

(86) PCT No.: PCT/FR2009/050498
§ 371 (c)(1),
(2), (4) Date: Nov. 16, 2010

(87) PCT Pub. No.: WO2009/125119
PCT Pub. Date: Oct. 15, 2009

(65) Prior Publication Data
US 2011/0197664 A1 Aug. 18, 2011

(30) Foreign Application Priority Data
Mar. 25, 2008 (FR) ...................................... 08 01601

(51) Int. Cl.
*G01N 13/02* (2006.01)
(52) U.S. Cl.
USPC ......................................... 73/64.55; 73/64.48
(58) Field of Classification Search
USPC ................... 73/64.48–64.52, 64.55
See application file for complete search history.

(56) References Cited

U.S. PATENT DOCUMENTS

| | | | |
|---|---|---|---|
| 3,030,802 A | | 4/1962 | Aarts et al. |
| 3,836,912 A | * | 9/1974 | Ghougasian et al. ........... 347/81 |
| 3,913,385 A | * | 10/1975 | Jobe ............................. 73/61.43 |
| 4,196,615 A | * | 4/1980 | Davis .......................... 73/64.52 |

(Continued)

FOREIGN PATENT DOCUMENTS

| | | |
|---|---|---|
| GB | 1317200 | 5/1973 |
| GB | 2408572 A | 6/2005 |

OTHER PUBLICATIONS

Guillot et al., "Stability of a Jet in Confined Pressure-Driven Biphase Flows at Low Reynolds Numbers", Physical Review Letters, 2007, pp. 104501(1)-104502(4), vol. 99, The American Physical Society.

(Continued)

*Primary Examiner* — John Fitzgerald
(74) *Attorney, Agent, or Firm* — Dentons US LLP

(57) ABSTRACT

The interfacial tension between two liquids is determined by: flowing an internal liquid ($L_i$) through an internal flow member (2) and flowing an external liquid ($L_e$) through an external flow member (4), with conditions being first established such that either droplets (G) of the internal liquid are formed in the external liquid, or a continuous jet of the internal liquid is formed in the external liquid, the continuous jet of the internal liquid then being formed in the external liquid or droplets of the internal liquid then being formed in the external liquid, and deducing therefrom the value of the interfacial tension between these two liquids.

15 Claims, 2 Drawing Sheets

(56) References Cited

U.S. PATENT DOCUMENTS

| | | | | |
|---|---|---|---|---|
| 4,294,800 | A | * | 10/1981 | Tavlarides et al. ............... 422/50 |
| 4,569,226 | A | * | 2/1986 | Matteson ...................... 73/64.52 |
| 4,697,451 | A | * | 10/1987 | Matteson ...................... 73/64.52 |
| 4,874,426 | A | | 10/1989 | Honda |
| 5,218,841 | A | * | 6/1993 | Hool ............................ 73/64.52 |
| 5,394,740 | A | * | 3/1995 | Schramm et al. ............ 73/64.48 |
| 5,542,289 | A | * | 8/1996 | Hool et al. ................... 73/64.52 |
| 5,559,284 | A | | 9/1996 | Matta et al. |
| 2003/0205079 | A1 | | 11/2003 | Taylor |

OTHER PUBLICATIONS

Utada et al., "Absolute Instability of a Liquid Jet in a Coflowing System", Physical Review Letters, 2008, pp. 014502(1)-014502(4), vol. 100, The American Physical Society.

Ronay "Determination of the Dynamic Surface Tension of Inks from the Capillary Instability of Jets", Journal of Colloid and Interface Science, 1978, pp. 55-67, vol. 66.

Sato et al., "Surface Tension Reduction of Liquid by Applied Electric Field Using Vibrating Jet Method", IEEE Transactions on Industry Applications, 1998, pp. 294-300, vol. 34, No. 2.

* cited by examiner

METHOD AND APPARATUS FOR DETERMINING THE INTERFACIAL TENSION BETWEEN TWO LIQUIDS

CROSS-REFERENCE TO PRIOR APPLICATIONS

This application is a continuation of PCT/FR 2009/050498, filed Mar. 24, 2009 and designating the United States (published in the French language on Oct. 15, 2009, as WO 2009/125119 A1; the title and abstract were also published in English), which claims foreign priority under 35 U.S.C. §119 of FR 0801601, filed Mar. 25, 2008, each hereby expressly incorporated by reference in its entirety and each assigned to the assignee hereof.

The present invention relates to a method for determining the interfacial tension between two liquids, to a facility for implementing this method and to a screening method comprising such a method of determination.

When two immiscible liquids are brought into contact with each other, it is necessary to supply energy to increase their contact area. If the amount of this energy is small, these two liquids flow in the form of two respective jets. If this energy is progressively increased, these two liquids end up forming droplets. The energy per unit area that it is necessary to supply in order to form such droplets is called the interfacial tension between the two liquids in question.

It is very important in many technological sectors to know this interfacial tension. Thus, by way of nonlimiting example, the following technologies may be mentioned: chemical processes, inkjet printing, spray drying, emulsification processes and the extrusion of polymers.

The prior art already discloses several methods for determining this interfacial tension.

A first solution, using what is called the weighed droplet method, consists in collecting a specified number of droplets, from a capillary tube, in a container. By weighing the container, the average weight of each droplet is then deduced and the interfacial tension then calculated from this weight and from the radius of the capillary tube used.

An alternative solution, called the spinning drop method, consists in pouring a drop into a container and then spinning it, subjecting it to a centrifugal force. The interfacial tension is deduced from various parameters, such as especially the shape adopted by the drop while it is being rotated.

However, these known solutions have certain drawbacks. Thus, they often prove to be tedious to implement. In addition, each method of determination is limited to a relatively narrow range of measurements.

In this regard, the weighed-drop method addresses more particularly the study of liquids having high interfacial tensions, typically greater than 5 mN/m. On the other hand, the spinning drop method is suitable only for very low interfacial tensions, typically less than 0.1 mN/m.

This being the case, the invention aims to remedy the various drawbacks. The object of the invention is in particular to provide a method for determining, in a reliable and simple manner, the interfacial tension between two liquids. Another object of the invention is to provide such a method which can be implemented for a very wide range of interfacial tensions. A final object of the invention is to provide such a process which allows the interfacial tension to be determined for many pairs of liquids, especially by virtue of a rapid change in the composition of said liquids.

For this purpose, one subject of the invention is a method for determining at least one value of the interfacial tension between two liquids, comprising the following steps:

a first liquid, called internal liquid, is made to flow in an internal flow member and a second liquid, called external liquid, is made to flow in an external flow member, the respective internal and external flow members being coaxial and the internal member opening into the internal volume of the external flow member;

conditions are firstly set up so that, downstream of the outlet of the internal flow member in the external flow member,
 i) either droplets of the internal liquid are formed in a carrier phase P formed by the external liquid
 ii) or a continuous jet of the internal liquid is formed in the external liquid;

the flow rate of at least one of the two liquids is varied;

a pair of liquid flow rate values, called transition values, is identified, from which:
 i) either a continuous jet of the internal liquid is then formed in the external liquid
 ii) or droplets of the internal liquid are then formed in the external liquid; and the interfacial tension between these two liquids is deduced therefrom.

According to other features:

the diameter of the internal flow member is between 10 microns and 2 millimeters, in particular between 10 and 200 microns, whereas the diameter of the external flow member is between 50 microns and 4 millimeters, preferably between 100 and 500 microns;

the ratio of the diameter of the external flow member to the diameter of the internal flow member is between 1.2 and 10, preferably between 1.5 and 5;

the two liquids are made to flow with flow rates of between 1 microliter per hour and 100 ml per hour, preferably between 10 and 10 000 microliters per hour;

the flow rate of the external liquid, called the external flow rate, is fixed and the flow rate of the internal liquid, called the internal flow rate, is varied;

the value of the interfacial tension is deduced from the fixed external liquid flow rate, from the transition flow rate of the internal liquid, from the diameter of the external capillary and from the viscosities of the internal and external liquids;

to deduce this interfacial tension value, the following equation is used:

$$Ka x^3 E(x, \lambda) = CF(x, \lambda) \text{ in which}$$

$$C = \frac{5 + \sqrt{7}}{18} \sqrt{\frac{24}{\sqrt{7} - 1}},$$

$$E(x, \lambda) = -4x + (8 - 4\lambda^{-1})x^3 + 4(\lambda^{-1} - 1)x^{-5},$$

$$F(x, \lambda) = x^4(4 - \lambda^{-1} + 4\ln(x)) + x^6(-8 + 4\lambda^{-1}) + x^8(4 - 3\lambda^{-1} - (4 - 4\lambda^{-1})\ln(x)),$$

$$\lambda = \frac{\eta_i}{\eta_e},$$

$$\alpha = \sqrt{\left(1 + \lambda^{-1}\frac{Qi}{Qe}\right)},$$

$$x = \frac{2rj}{De} = \sqrt{\frac{\alpha - 1}{\lambda^{-1} + \alpha - 1}},$$

$$Ka = \frac{\Delta P D_e^2}{\gamma^4}, \text{ with}$$

-continued $$\Delta P = \frac{128\eta_e Q_e}{\pi D_e^4 (1-x^2)}$$

several values of the interfacial tension between the same two liquids are determined by fixing various external flow rates in succession and then, for each of these values thus fixed, by varying the internal flow rates;

a surfactant is added to the two liquids, the time of formation of the droplets is varied, several values of the interfacial tension between these two same liquids, relative to different droplet formation times, are determined, a curve representing the variation of these interfacial tension values as a function of the droplet formation time is produced and a characteristic time of the surfactant, corresponding to the transition between a zone in which the interfacial tension is approximately constant as a function of the formation time and an adjacent zone in which this interfacial tension increases as this formation time decreases, is identified; and the existence of droplets or the existence of a jet is identified by placing a laser emitter and a photodiode on either side of the external flow member, downstream of the outlet of the internal flow member.

Another subject of the invention is a facility for implementing the method as described above, comprising:

an internal flow member and an external flow member, which are coaxial, the internal flow member opening into the internal volume of the external flow member;

means for feeding the two flow members with the two liquids respectively;

means for varying the flow rate of at least one of the liquids; and means for observing the flow of the first liquid in the second liquid.

The final subject of the invention is a method of screening various pairs of liquids, in which these various pairs of liquids are prepared, at least one interfacial tension relative to each of these pairs of liquids is determined, using the above method, and at least one preferred pair of liquids is identified from said several pairs of liquids.

According to other features:

the various pairs of liquids are prepared by adding at least one substance to at least one liquid, this substance being especially a surfactant and/or a polymer and/or a solid particle; and the various pairs of liquids are prepared by modifying at least one condition of at least one liquid, in particular the pH and/or the temperature and/or the pressure thereof.

The invention is described below with reference to the appended drawings, given solely by way of nonlimiting examples, in which.

Figure 1:
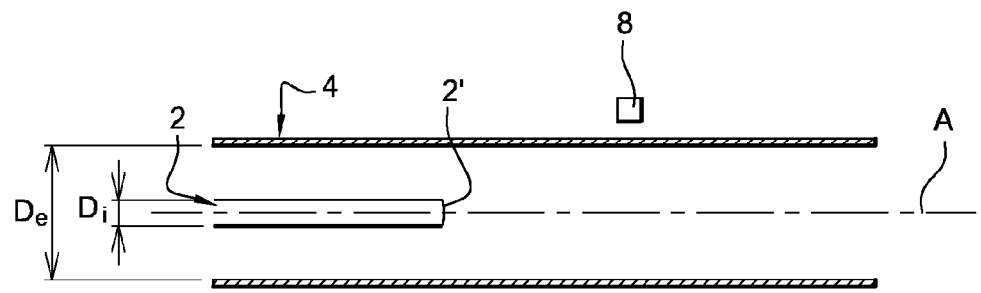
FIG. 1 is a side view, illustrating a facility for implementing a method for determining the interfacial tension between two liquids, in accordance with the invention.

The facility according to the invention, illustrated in FIG. 1, comprises two flow members, namely an internal flow member 2 and an external flow member 4. These flow members are for example capillary tubes, in particular made of glass, treated glass, PTFE or another plastic.

These two capillary tubes 2 and 4 are advantageously coaxial and thus have a common principal axis, denoted by A. Moreover, the external diameter of the internal capillary tube 2 is denoted by $D_i$, this diameter including the capillary tube walls. The internal diameter of the external capillary tube 4 is denoted by $D_e$, this diameter however not including the walls of the capillary tube 4.

Advantageously, $D_i$ is between 10 microns (or micrometers) and 2 millimeters, preferably between 10 microns and 200 microns, whereas $D_e$ is between 50 microns and 4 millimeters, preferably between 100 microns and 500 microns. Furthermore, the $D_e/D_i$ ratio is advantageously between 1.2 and 10, preferably between 1.5 and 5.

The outlet of the internal capillary tube 2, in the internal volume of the external capillary tube 4, is denoted by 2'. Provided immediately downstream of this outlet 2', on a first side of the capillary tube 4, is a laser emitter 6 with which a photodiode 8, placed opposite this emitter 6, is associated. As will be seen in what follows, this emitter and this photodiode are capable of delivering a signal for obtaining information about the droplet formation and about the frequency of this formation.

The facility described above, with reference to FIG. 1, allows a method according to the invention, for determining the interfacial tension between two liquids, to be implemented. For this purpose, the capillary tubes 2 and 4 are brought into communication with means for supplying two immiscible liquids to be tested. These supply means, which are of conventional type, have not been shown in the figures. Usually, these means are for example microfluidic syringes and connectors.

The method starts by setting the external flow rate, denoted by $Q_e(1)$, of the liquid $L_e$ flowing in the external capillary tube. Advantageously, this external flow rate is between 1 microliter/hour and 100 ml/hour, preferably between 10 microliters/hour and 10 000 microliters/hour. In addition, the external flow rate, denoted by $Q_i$, of the liquid $L_i$ flowing in the internal capillary tube is set at a very low value. Under these conditions, when the two immiscible liquids come into contact with each other, droplets G of the internal liquid are formed in a carrier phase P, formed by the external liquid (see FIG. 2).

Next, for the same external flow rate $Q_e(1)$, the flow rate $Q_i$ is progressively increased according to a predetermined function $Q_i=f(t)$ as a function of time. The signal emitted by the photodiode as a function of time is then observed.

Figure 2:
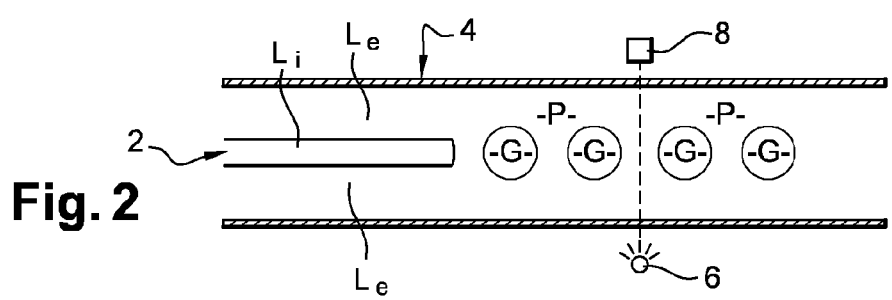
FIGS. 2, 4 and 5 are side views, similar to FIG. 1, illustrating various steps for implementing this method.
Figure 4:
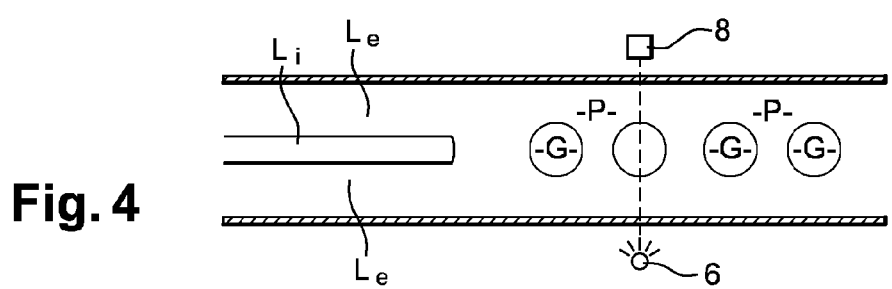
Figure 3:
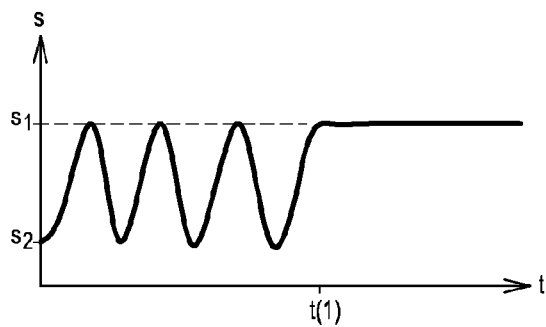
FIG. 3 is a graph illustrating the variations in the signal from a photodiode as a function of time.

At the start of flow of the two liquids, corresponding to the formation of droplets, the signal is periodic, that is to say it oscillates between two values, $s_1$ and $s_2$ respectively (see FIG. 3). The value $s_1$ corresponds to the position in which the laser and the photodiode are separated both by the internal liquid and the external liquid (FIG. 4), whereas the signal $s_2$ corresponds to the position for which the laser and the photodiode are separated only by the external liquid (FIG. 2).

Figure 5:
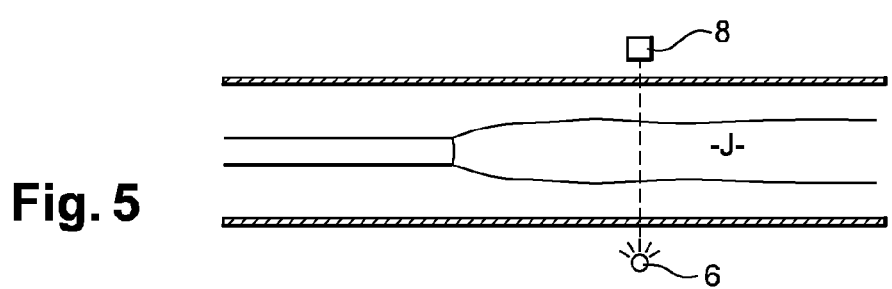

It should be noted that, above a certain value of the flow rate $Q_i$, the droplets initially produced are replaced by a continuous jet J of the internal liquid in the external liquid (FIG. 5). After this threshold value has been reached, the signal emitted by the photodiode stabilizes to the value $s_1$ since the laser and the photodiode are permanently separated both by the internal liquid and the external liquid.

The curve shown in FIG. 3 identifies the instant, denoted by $t(1)$, that corresponds to the appearance of the continuous jet. Given that, as mentioned above, the variation in flow rate $Q_i$ is known as a function of time, a flow rate $Q_i(1)$ corresponding to this instant $t(1)$ of jet formation may be obtained. Knowing the external flow rate $Q_e(1)$ and the internal flow rate $Q_i(1)$ for which the continuous jet appears, it is possible to deduce therefrom the interfacial tension $\gamma(1)$ between the two liquids.

For this purpose, the following equation is used:

$$Ka\alpha^3 E(x, \lambda) = CF(x, \lambda) \text{ in which}$$

$$C = \frac{5 + \sqrt{7}}{18} \sqrt{\frac{24}{\sqrt{7} - 1}},$$

$$E(x, \lambda) = -4x + (8 - 4\lambda^{-1})x^3 + 4(\lambda^{-1} - 1)x^{-5},$$

$$F(x, \lambda) =$$
$$x^4(4 - \lambda^{-1} + 4\ln(x)) + x^6(-8 + 4\lambda^{-1}) + x^8(4 - 3\lambda^{-1} - (4 - 4\lambda^{-1})\ln(x)),$$

$$\lambda = \frac{\eta_i}{\eta_e},$$

$$\alpha = \sqrt{\left(1 + \lambda^{-1} \frac{Qi}{Qe}\right)}, \text{ and}$$

$$x = \frac{2rj}{De} = \sqrt{\frac{\alpha - 1}{\lambda^{-1} + \alpha - 1}}.$$

By solving the above equation (1) it is possible to obtain the value of Ka and then that of $\gamma$ using the following equation:

$$Ka = \frac{\Delta P D_e^2}{\gamma^4}, \text{ with}$$

$$\Delta P = \frac{128 \eta_e Q_e}{\pi D_e^4 (1 - x^2)}$$

As is apparent from the foregoing, this interfacial tension may be deduced by knowing only the fixed external liquid flow rate $Q_e$, the transition internal liquid flow rate $Q_i$, the external capillary tube diameter $D_e$, and the viscosities $\eta_i$ and $\eta_e$ of the internal and external liquids. This interfacial tension can therefore be simply and rapidly determined.

The operation described above may be repeated, each time setting the external flow rate $Q_e$ to different values, denoted by $Q_e(2)$ to $Q_e(n)$. This makes it possible to obtain corresponding internal flow rate values, denoted by $Q_i(2)$ to $Q_i(n)$, for which the transition between droplets and jet takes place. For each group of flow rates $Q_i(j)$ and $Q_e(j)$, in which j varies from 1 to n, it is also possible to deduce n interfacial tensions denoted by $\gamma(1)$ to $\gamma(n)$. The internal flow rates $Q_i$ are typically between 1 microliter/hour and 100 ml/hour, especially between 10 microliters/hour and 10 000 microliters/hour.

Figure 6:
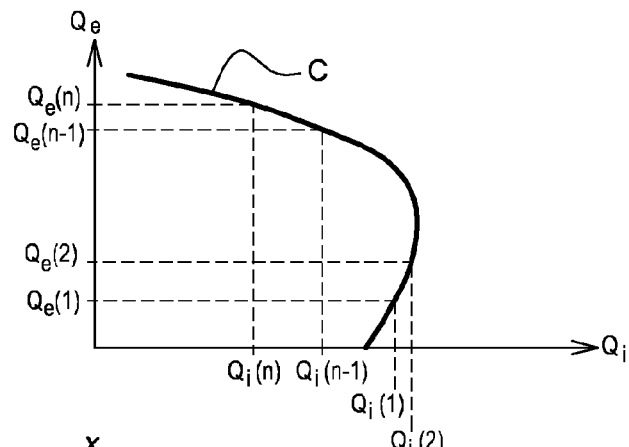
FIGS. 6 and 8 are curves illustrating various transition flow rates obtained in accordance with the invention.

Moreover, FIG. 6 shows the various flow rates $Q_e$ and $Q_i$, on the one hand those that are set and, on the other hand, those that are determined according to the above steps. Curve C joins the various experimentally determined values of the internal flow rate. Thus, to the left of this curve, the internal and external flow rates are such that the flow of the two liquids results in the formation of droplets of the internal liquid in the external liquid. In contrast, to the right of this curve, said flow leads to the formation of a continuous jet of the internal liquid in the external liquid. It is advantageous to obtain this curve C since it enables the uncertainty of the measurement to be checked.

As a variant, for a fixed external flow rate, a very high initial internal flow rate may be chosen so that the contacting between the two liquids results in the formation of a jet. In other words, the initial situation corresponds to the right of curve C in FIG. 6 and not to the left, as in the first embodiment.

The internal flow rate is then progressively reduced until droplets are obtained. Similarly to what was described above, the internal flow rate sought corresponds to that for which the jet-to-droplet transition is identified and not the droplet-to-jet transition, as in the first embodiment illustrated in FIG. 2.

As a variant, it is conceivable to fix not the external flow rate but the internal flow rate, so that in this case it is the external flow rate that is then varied. This may be advantageous, so as to reduce the measurement errors, especially by firstly carrying out a first series of measurements with a fixed external flow rate and then a second series with a fixed internal flow rate, for the same liquids. An average of the values obtained from these two series of measurements may then be advantageously obtained.

According to an advantageous variant of the invention, it is possible to screen various pairs of liquids by using the method of determining surface tension as described above.

For this purpose, the capillary flow tubes 2 and 4 are connected with means for adding at least one substance to at least one liquid, and/or with means for modifying the flow conditions of at least one of these liquids. The addition means are used to add, to one or both of the liquids, various types of substances, such as a surfactant, a polymer, solid particles, salts, acids or bases. The means for modifying the flow conditions are for example capable of varying the pH, the temperature or the pressure.

Next, a pair of liquids, called base liquids, is prepared, the surface tension between which is determined in accordance with the method described above. The base pair is then modified by adding at least one substance to at least one liquid and/or by modifying at least one condition of at least one of these base liquids.

The various surface tensions, relative to the various pairs of liquids thus prepared, are then determined. Finally, one or more preferred pairs of liquids, for example those having the lowest surface tension therebetween, are determined.

Figure 7:
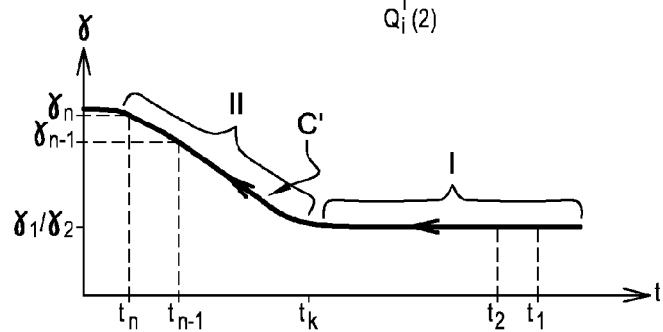
FIG. 7 is a graph illustrating the variation in the surface tension as a function of the droplet formation time.

FIG. 7 illustrates an advantageous variant of the invention, in which various values of the interfacial tension as a function of the rate of droplet formation are measured. As will be seen later, this enables the rate of adsorption of a surfactant at the interface between the liquids, namely the dynamic interfacial tension, to be determined.

The same facility as that described in FIG. 1 is used, however it should be noted that a surfactant, the properties of which it is desired to determine, is made to flow therein. This surfactant is added, as is usual, to one or both of the liquids.

In the first step of this implementation variant, the external flow rate $Q_e$ is set to a very low value, denoted by $Q_e(1)$. In this way it is possible to ensure that the surfactant has the time needed to be adsorbed at the interface between the two liquids.

The internal liquid is then made to flow at a very low initial flow rate, and this flow rate is progressively increased according to the procedure described above. The internal flow rate above which the droplets are transformed into a continuous jet is denoted by $Q_i(1)$.

Moreover, the frequency of formation of these droplets, which is very low because of the very low flow rate $Q_e(1)$, is denoted by $\omega_1$. This formation frequency is measured for example by the laser emitter 6 associated with the photodiode 8. Finally, the interfacial tension $\gamma_1$ is calculated from the above flow rates $Q_e(1)$ and $Q_i(1)$ using equation (1).

In a second step, the external flow rate is set to a value $Q_e(2)$ greater than $Q_e(1)$ above. Consequently, the droplet formation frequency $\omega_2$ will be greater than the frequency $\omega_1$ mentioned above. Next, similarly to the first step, the flow rate $Q_i$ is varied until a value $Q_i(2)$ corresponding to the transition between droplets and continuous jet is identified. This enables a second interfacial tension denoted by $\gamma_2$ to be obtained.

These two steps are repeated, iteratively, for n flow rate values, thereby making it possible to obtain n droplet formation frequency values and n interfacial tension values.

The variation of the interfacial tension $\gamma$ is plotted in FIG. 7 as a function of the droplet formation time t, which corresponds to the inverse of the frequency $\omega$. In this figure, the values $t_1, t_2, t_{n-1}, t_n$ and $\gamma_1, \gamma_2, \gamma_{n-1}$ and $\gamma_n$ are shown.

It can be seen that the curve C' thus obtained is divided into two main regions. Thus, a first region I corresponds to long formation times and consequently to short production frequencies, for which the interfacial tension $\gamma$ is approximately constant. In other words, in this portion of the curve, the droplets form sufficiently slowly to allow the surfactant to be adsorbed at the interface between the two liquids.

There is then a region II corresponding to higher formation frequencies, namely to shorter formation times. On approaching the minimum formation time $t_n$, it is noted that the interfacial tension $\gamma$ increases. In other words, the more the droplets form at higher frequencies, the less time the surfactant has to be adsorbed and, consequently, the more the interfacial tension increases.

A transition point denoted by $t_K$ is identified at the intersection between the regions I and II, this point corresponding to the minimum characteristic time needed for the surfactant to be adsorbed at the interface between the two liquids. In other words, the time $t_K$ is a characteristic of the surfactant being studied in that it corresponds to the minimum duration required for this surfactant to be adsorbed at the interface between the two liquids.

Based on this embodiment, as described immediately above, it is possible to implement a method of screening various surfactants. For this purpose, two immiscible base liquids are used that are made to flow in the capillary tubes 2 and 4. Various surfactants, the characteristic times $t_K$ of which are measured using the steps described above, are then added in succession thereto. The preferred surfactant(s) corresponds (correspond) in particular to those having characteristic times shorter than the characteristic times of the application. Typically, the characteristic time for spray additives is of the order of one millisecond whereas that for detergent additives is of the order of one second.

This screening of surfactants may be carried out advantageously in many technical fields, such as those of detergents or spray additives. Thus, in the case of detergents, the two liquids that are made to flow are, for example, oil and water, while the surfactants studied are of the sulfonate family or non-ionic surfactants.

The invention makes it possible to achieve the abovementioned objectives.

Specifically, the method of determining the interfacial tension, in accordance with the invention, may be carried out in a simple and rapid manner. Furthermore, the various steps involved can be carried out in an automated manner, at least for most of them.

In addition, the method of the invention enables a wide range of interfacial tension values to be measured. Furthermore, it is possible for the nature of the two liquids, the interfacial tension between which it is desired to determine, to be varied very rapidly.

Finally, the facility according to the invention, for implementing the above method, is inexpensive since it involves a small number of components and has a simple structure.

The invention will be illustrated below, in the light of the following embodiment, in a purely nonlimiting example.

Two coaxial capillary tubes are used, the external capillary tube having a diameter of 500 microns while the internal capillary tube has a diameter of 300 microns. Two immiscible liquids, namely dodecane as external liquid and water as internal liquid, are made to flow in the two capillary tubes. The respective viscosities of said liquids are $1.29 \times 10^{-3}$ Pa·s and $1 \times 10^{-3}$ Pa·s.

Various dodecane flow rates in the external capillary tube are set between 0.001 and 100 microliters/second. For each of these flow rates, the internal flow rate of water is increased according to the process described above. For low internal flow rates, water droplets form in the dodecane, and then, above a transition internal flow rate, these droplets are transformed into a continuous water jet in the dodecane.

Figure 8:
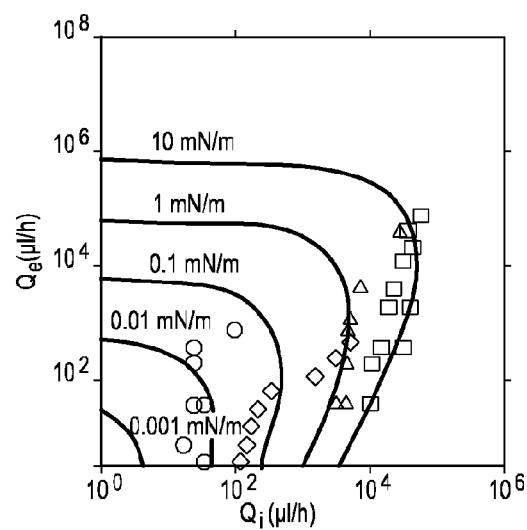

Various transition internal flow rates are deduced from this, as plotted on the curve shown in FIG. 8 in which they are indicated by squares. Surface tensions between 30 and 50 mN/m are deduced from this using the equations presented above.

The above operating mode is repeated but with a surfactant denoted by A, of the phosphate ester type sold by the company Rhodia, being added in an amount of 2% by weight to the water and to the dodecane. This makes it possible to obtain various points identified by triangles. The identified surface tensions are between 3 and 6 mN/m.

The above process is then repeated, this time changing the nature of the surfactant. Surfactant A used above is replaced with a mixture of 2% by weight of said surfactant A to which 4% by weight of sec-butanol is added. By carrying out the same process as above, various transition flow rates, identified by diamond symbols, are obtained. The identified surface tensions are between 0.06 and 0.08 mN/m.

Finally, the same experiment is repeated, again modifying the nature of the surfactant. Thus, a 50/50 mixture of surfactant A above and of a surfactant B, different from surfactant A but of similar nature, is firstly used. 2% by weight of this mixture and 4% by weight of sec-butanol are added. Thus, various transition flow rates identified by circles are obtained. The extracted surface tensions are around 0.008 mN/m.

FIG. 8 shows, apart from the experimental points presented above, the various theoretical curves available in the literature. It may be seen that the experimental points are relatively close to these curves, thereby confirming the consistency of the measurements carried out. Where appropriate, these experimental curves may be adjusted so as to deduce therefrom one or more surface tension values.

The invention claimed is:

1. A method for determining the dynamic interfacial tension of a surfactant between two liquids, comprising the following steps:

flowing a first liquid, the internal liquid (Li), in an internal flow member (2);

flowing a second liquid, the external liquid (Le), in an external flow member (4); and, adding a surfactant to the one and/or other of the first and second liquids;

wherein the respective internal and external flow members are coaxial and the internal member opens into the internal volume of the external flow member;

forming droplets (G) of the internal liquid, in a carrier phase (P) formed by the external liquid, downstream of the outlet (2') of the internal flow member in the external flow member, under conditions set for a plurality of values of flow rate (Qe), the flow rate of the external liquid; and determining the value of time (t) of formation of these droplets;

subsequently varying the internal flow rate (Qi); and after identifying a transition value of the internal flow rate above which a continuous jet of the internal liquid is then formed in the external liquid, deducing therefrom a value of the interfacial tension (γ) between these two liquids; and producing a curve representing the variation of the interfacial tension value as a function of the droplet formation time; and identifying a characteristic time ($t_k$) of the surfactant, corresponding to the transition between a first zone (I) in which the value of the interfacial tension is approximately constant as a function of the droplet formation time and a second zone (II) in which this value of the interfacial tension increases as this formation time decreases.

2. The method of determination as defined by claim 1, wherein existence of droplets (G) is identified by placing a laser emitter (6) and a photodiode (8) on either side of the external flow member (4), downstream of the outlet (2') of the internal flow member (2).

3. The method as defined by claim 1, wherein, for each of the values of the external flow rate (Qe), the value of the time (t) of formation of the droplets corresponds to the inverse of the frequency (ω) of formation of the droplets, that is measured.

4. The method as defined by claim 3, wherein existence of droplets (G) is identified by placing a laser emitter (6) and a photodiode (8) on either side of the external flow member (4), downstream of the outlet (2') of the internal flow member (2), and wherein the frequency (ω) of formation of the droplets is measured by the laser emitter (6) and the photodiode (8).

5. The method as defined by claim 1, wherein the value of each interfacial tension value (γ) is deduced from the value of the external flow rate, from the value of transition of the internal flow rate, from the diameter of the external (De) capillary and from the viscosities (η) of the internal and external liquids.

6. The method as defined by claim 5, wherein, the interfacial tension value is deduced using the following equation:

$$Kax^3 E(x, \lambda) = CF(x, \lambda) \text{ in which}$$

$$C = \frac{5 + \sqrt{7}}{18} \sqrt{\frac{24}{\sqrt{7} - 1}},$$

$$E(x, \lambda) = -4x + (8 - 4\lambda^{-1})x^3 + 4(\lambda^{-1} - 1)x^{-5},$$

$$F(x, \lambda) =$$

-continued
$$x^4(4 - \lambda^{-1} + 4\ln(x)) + x^6(-8 + 4\lambda^{-1}) + x^8(4 - 3\lambda^{-1} - (4 - 4\lambda^{-1})\ln(x)),$$

$$\lambda = \frac{\eta_i}{\eta_e},$$

$$\alpha = \sqrt{\left(1 + \lambda^{-1} \frac{Qi}{Qe}\right)},$$

$$x = \frac{2rj}{De} = \sqrt{\frac{\alpha - 1}{\lambda^{-1} + \alpha - 1}},$$

$$Ka = \frac{\Delta P D_e^2}{\gamma^4}, \text{ with}$$

$$\Delta P = \frac{128 \eta_e Q_e}{\pi D_e^4 (1 - x^2)}.$$

7. The method as defined by claim 1, wherein the diameter of the internal flow member ranges from 10 microns to 2 millimeters and that of the external flow member ranges from 50 microns to 4 millimeters.

8. The method as defined by claim 7, wherein the diameter of the internal flow member ranges from 10 to 200 microns, and the diameter of the external flow member ranges from 100 to 500 microns.

9. The method as defined by claim 1, wherein the ratio of the diameter of the external flow member to the diameter of the internal flow member ranges from 1.2 to 10.

10. The method as defined by claim 9, wherein the ratio of the diameter of the external flow member to the diameter of the internal flow member ranges from 1.5 to 5.

11. The method as defined by claim 1, wherein the two liquids flow at flow rates ranging from 1 microliter per hour to 100 ml per hour.

12. The method as defined by claim 11, wherein the two liquids flow at flow rates ranging from 10 to 10,000 microliters per hour.

13. A method of screening various surfactants, wherein the method comprises, preparing two immiscible base liquids;

adding in succession various surfactants to the two immiscible base liquids;

determining the interfacial tension value relative to each of these surfactants using the method as defined by claim 1; and identifying at least one preferred surfactant from various surfactants according the characteristic time ($t_k$) thereof.

14. The screening method as defined by claim 13, wherein the two base liquids are oil and water, and the screened surfactants are sulfonates.

15. The screening method as defined by claim 13, wherein the two base liquids are oil and water, and the screened surfactants are non-inonic surfactants.

* * * * *